US010738363B2

(12) United States Patent
Ma et al.

(10) Patent No.: US 10,738,363 B2
(45) Date of Patent: Aug. 11, 2020

(54) ANALYZER AND ANALYTICAL METHOD FOR PREDICTING PROGNOSIS OF CANCER RADIOTHERAPY

(71) Applicants: National Central University, Taoyuan (TW); Huan-Cheng Chang, Taoyuan (TW)

(72) Inventors: Nian-Han Ma, Taoyuan (TW); Tao-Sheng Chung, Taipei (TW); An-Lun Li, Miaoli County (TW); Yao-Ning Chan, Taoyuan (TW); Chien-Lung Chen, New Taipei (TW)

(73) Assignees: NATIONAL CENTRAL UNIVERSITY, Taoyuan (TW); Huan-Cheng Chang, Taoyuan (TW)

( * ) Notice: Subject to any disclaimer, the term of this patent is extended or adjusted under 35 U.S.C. 154(b) by 338 days.

(21) Appl. No.: 15/691,730

(22) Filed: Aug. 30, 2017

(65) Prior Publication Data

US 2018/0057891 A1    Mar. 1, 2018

(30) Foreign Application Priority Data

Aug. 31, 2016   (TW) ............................. 105128099 A
Jul. 17, 2017   (TW) ............................. 106123853 A (51) Int. Cl.
     *C12Q 1/6886*      (2018.01)

(52) U.S. Cl.
     CPC ..... *C12Q 1/6886* (2013.01); *C12Q 2600/106* (2013.01); *C12Q 2600/118* (2013.01); *C12Q 2600/158* (2013.01); *C12Q 2600/178* (2013.01)

(58) Field of Classification Search
     CPC .................................................. C12Q 1/6886
     USPC .......................................................... 702/19
     See application file for complete search history.

(56) References Cited

U.S. PATENT DOCUMENTS

| 2008/0311039 A1 | 12/2008 | Bonavida et al. |
| 2015/0011414 A1 | 1/2015 | Johansen et al. |

FOREIGN PATENT DOCUMENTS

| CN | 105200043 A | 12/2015 |
| CN | 102369530 B | 5/2016 |
| EP | 2502630 A2 | 9/2012 |
| KR | 20120092345 A | 8/2012 |
| TW | 200503653 A | 2/2005 |
| TW | 200711659 A | 4/2007 |
| TW | I367949 B | 7/2012 |
| TW | 201309805 A | 3/2013 |
| TW | 201309807 A | 3/2013 |
| TW | 201413245 A | 4/2014 |
| TW | 201418472 A | 5/2014 |
| TW | I461540 B | 11/2014 |
| TW | I546075 B | 8/2016 |
| WO | 99/12039 A1 | 3/1999 |
| WO | 2012135814 A2 | 10/2012 |
| WO | 2012135817 A2 | 10/2012 |
| WO | 2013190091 A1 | 12/2013 |
| WO | 2014130617 A1 | 8/2014 |
| WO | 2014201542 A1 | 12/2014 |

OTHER PUBLICATIONS

Xiao-Chun Wang et al., "Expression and function of miRNA in postoperative radiotherapy sensitive and resistant patients of non-small cell lung cancer", Lung Cancer, vol. 72, Issue 1, 2011, pp. 92-99.

Richard Hummel et al., "MicroRNAs: Predictors and modifiers of chemo-and radiotherapy in different tumour types", European Journal of Cancer, vol. 46, 2010, pp. 298-311.

Kyung Min Lee et al., "microRNA-7 increases radiosensitivity of human cancer cells with activated EGFR-associated signaling", Radiotherapy and Oncology, 101 (2011), pp. 171-176.

Thomas Templin et al., "Radiation-induced micro-RNA expression changes in peripheral blood cells of radiotherapy patients", International Journal of Radiation Oncology Biology Physics, vol. 80, No. 2, pp. 549-557, 2011.

*Primary Examiner* — Jerry Lin
(74) *Attorney, Agent, or Firm* — CKC & Partners Co., LLC (57) ABSTRACT

The present invention provides an analyzer for predicting a prognosis of cancer radiotherapy, including a detection device and an arithmetic device. In a specimen, expression levels of a plurality of microRNAs (miRNAs) can be detected by the detection device. The miRNAs includes hsa-miR-130a-3p, hsa-miR-215-5p, hsa-miR-29a-3p, hsa-let-7b-5p, hsa-miR-19b-3p, hsa-miR-374a-5p and hsa-miR-148a-3p. The expression levels of miRNAs can be analyzed by the arithmetic device using logistic regression, and the analyzed values can be used to determine that the prognosis of cancer radiotherapy is poor or good.

18 Claims, 4 Drawing Sheets

Specification includes a Sequence Listing.

ANALYZER AND ANALYTICAL METHOD FOR PREDICTING PROGNOSIS OF CANCER RADIOTHERAPY

This application claims priority to Taiwan Application Serial Number 105128099, filed Aug. 31, 2016 and Taiwan Application Serial Number 106123853, filed Jul. 17, 2017, which are herein incorporated by reference.

BACKGROUND

Field of Invention

The present invention relates to an analyzer and analytical method for the prognosis of cancer. More particularly, the present invention relates to an analyzer and analytical method for predicting the prognosis of cancer radiotherapy.

Description of Related Art

Cancer (also called malignant tumor) refers to the abnormal cell proliferation causing physical organs to function improperly, and these proliferated cells may invade other organs nearby, or follow the blood and lymph and then metastasize throughout the body. Besides, cancer would lead to physical fatigue, weight loss, anemia, pain, weakness and depression, and is often accompanied by the infection of pathogens. More than twelve million people worldwide are diagnosed with cancer every year, and it should be realized that the treatment of cancer and prognosis thereof has become an urgent issue.

There are three main methods of cancer treatment: radiotherapy, chemotherapy, and surgery. Currently, about 50% of patients in all types of cancer require radiotherapy, but in some cases, it is noted that certain tumors are resistant to radiotherapy and prone to recurrence after radiotherapy, and thus result in the poor prognosis.

Therefore, there is an urgent need for an analyzer and analytical method for predicting the prognosis of cancer radiotherapy.

SUMMARY

To overcome the problems faced by the prior art, the present disclosure provides an analyzer for predicting a prognosis of cancer radiotherapy, including: a detection device and an arithmetic device. The detection device is configured to detect expression levels of a plurality of miRNAs in a specimen, wherein the plurality of miRNAs includes hsa-miR-130a-3p (SEQ ID NO:1), hsa-miR-215-5p (SEQ ID NO:2) and hsa-miR-29a-3p (SEQ ID NO:3). The arithmetic device is configured to perform arithmetic operations on the expression levels of the plurality of miRNAs, wherein (a) the expression level of hsa-miR-215-5p divided by the expression level of hsa-miR-130a-3p equals A, and if the A is less than or equal to 0.09723, X=1, and if the A is greater than 0.09723, X=0, (b) the expression level of hsa-miR-215-5p divided by the expression level of hsa-miR-29a-3p equals B, and if the B is less than or equal to 0.001005, Y=1, and if the B is greater than 0.001005, Y=0, and (c) Z represents a stage of the cancer, and the X, the Y, and the Z are substituted into equation (1):

$$-99.036+(39.434*X)+(59.996*Y)+(19.636*Z)=N \quad \text{equation (1)},$$

whereby the value of N is used to determine the prognosis is poor or good.

In various embodiments of the present disclosure, the analyzer further includes a judgment device configured to determine a prognosis result, wherein if N is greater than or equal to −10.51, the prognosis is poor, and if N is less than −10.51, the prognosis is good.

The present disclosure provides an analyzer for predicting a prognosis of cancer radiotherapy, including a detection device and an arithmetic device. The detection device is configured to detect expression levels of a plurality of miRNAs in a specimen, wherein the plurality of miRNAs includes hsa-miR-130a-3p (SEQ ID NO:1), hsa-let-7b-5p (SEQ ID NO:4), hsa-miR-19b-3p (SEQ ID NO:5) and hsa-miR-374a-5p (SEQ ID NO:6). The arithmetic device configured to perform on arithmetic operations on the expression levels of the plurality of miRNAs, wherein (a) the expression level of hsa-miR-130a-3p divided by the expression level of hsa-let-7b-5p equals A2, and if the A2 is greater than or equal to 0.07765, W=1, and if the A2 is less than 0.07765, W=0, (b) the expression level of hsa-miR-130a-3p divided by the expression level of hsa-miR-19b-3p equals B2, and if the B2 is greater than or equal to 0.004635, X2=1, and if the B2 is less than 0.004635, X2=0, (c) the expression level of hsa-miR-130a-3p divided by the expression level of hsa-miR-374a-5p equals C, and if the C is greater than or equal to 0.4640, Y2=1, and if the C is less than 0.4640, Y2=0, and (d) Z2 represents a stage of the cancer, and the W, the X2, the Y2, and the Z2 are substituted into equation (2):

$$-22.385+(0.113*W)+(18.555*X2)+(1.148*Y2)+(0.997*Z2)=N2 \quad \text{equation (2),}$$

whereby the value of N2 is used to determine the prognosis is poor or good.

In various embodiments of the present disclosure, the analyzer further includes a judgment device configured to determine a prognosis result, wherein if N2 is greater than or equal to 0.2145, the prognosis is poor, and if N2 is less than 0.2145, the prognosis is good.

In various embodiments of the present disclosure, wherein the specimen includes blood, urine, saliva or ascites.

In various embodiments of the present disclosure, wherein the specimen is obtained before the cancer radiotherapy.

The present disclosure provides an analytical method for predicting a prognosis of cancer radiotherapy, including: obtaining a plurality of miRNAs from a specimen, wherein the plurality of miRNAs includes hsa-miR-130a-3p (SEQ ID NO:1), hsa-let-7b-5p (SEQ ID NO:4), hsa-miR-19b-3p (SEQ ID NO:5) and hsa-miR-374a-5p (SEQ ID NO:6); detecting expression levels of the plurality of miRNAs from the specimen; and performing arithmetic operations on the expression levels of the plurality of miRNAs, wherein (a) (the expression level of hsa-miR-130a-3p)/(the expression level of hsa-let-7b-5p)=A2, and if the A2 is greater than or equal to 0.07765, W=1, and if the A2 is less than 0.07765, W=0, (b) (the expression level of hsa-miR-130a-3p)/(the expression level of hsa-miR-19b-3p)=B2, and if the B2 is greater than or equal to 0.004635, X2=L, and if the B2 is less than 0.004635, X2=0, (c) (the expression level of hsa-miR-130a-3p)/(the expression level of hsa-miR-374a-5p)=C, and if the C is greater than or equal to 0.4640, Y2=1, and if the C is less than 0.4640, Y2=0, and (d) Z2 represents a stage of the cancer, and the W, the X2, the Y2, and the Z2 are substituted into equation (2):

$$-22.385+(0.113*W)+(18.555*X2)+(1.148*Y2)+(0.997*Z2)=N2 \quad \text{equation (2),}$$

whereby the value of N2 is used to determine the prognosis is poor or good.

In various embodiments of the present disclosure, wherein if N2 is greater than or equal to 0.2145, the prognosis is poor, and if N2 is less than 0.2145, the prognosis is good.

In various embodiments of the present disclosure, wherein the specimen includes blood, urine, saliva or ascites.

In various embodiments of the present disclosure, wherein the specimen is obtained before the cancer radiotherapy.

The present disclosure provides an analyzer for predicting a prognosis of cancer radiotherapy, including a detection device and an arithmetic device. The detection device is configured to detect expression levels of a plurality of miRNAs in a specimen, wherein the plurality of miRNAs includes hsa-miR-130a-3p (SEQ ID NO:1), hsa-let-7b-5p (SEQ ID NO:4) and hsa-miR-148a-3p (SEQ ID NO:7). The arithmetic device is configured to perform arithmetic operations on the expression levels of the plurality of miRNAs, wherein (a) the expression level of hsa-miR-130a-3p divided by the expression level of hsa-let-7b-5p equals A3, and if the A3 is greater than or equal to 2.041, X3=1, and if the A3 is less than 2.041, X3=0, (b) the expression level of hsa-miR-130a-3p divided by the expression level of hsa-miR-148a-3p equals B3, and if the B3 is greater than or equal to 13.57, Y3=1, and if the B3 is less than 13.57, Y3=0, and (c) Z3 represents a stage of the cancer, and the X3, the Y3, and the Z3 are substituted into equation (3):

$$-10.939+(3.194*X3)+(2.330*Y3)+(2.159*Z3)=N3 \quad \text{equation (3)},$$

whereby the value of N3 is used to determine the prognosis is poor or good.

In various embodiments of the present disclosure, the analyzer further includes a judgment device configured to determine a prognosis result, wherein if N3 is greater than or equal to −0.6205, the prognosis is poor, and if N3 is less than −0.6205, the prognosis is good.

In various embodiments of the present disclosure, wherein the specimen includes blood, urine, saliva or ascites.

In various embodiments of the present disclosure, wherein the specimen is obtained after the cancer radiotherapy.

The present disclosure provides an analytical method for predicting a prognosis of cancer radiotherapy, including: obtaining a plurality of miRNAs from a specimen, wherein the plurality of miRNAs includes hsa-miR-130a-3p (SEQ ID NO:1), hsa-let-7b-5p (SEQ ID NO:4) and hsa-miR-148a-3p (SEQ ID NO:7); detecting expression levels of the plurality of miRNAs from the specimen; and performing arithmetic operations on the expression levels of the plurality of miRNAs, wherein (a) (the expression level of hsa-miR-130a-3p)/(the expression level of hsa-let-7b-5p)=A3, and if the A3 is greater than or equal to 2.041, X3=1, and if the A3 is less than 2.041, X3=0. (b) (the expression level of hsa-miR-130a-3p)/(the expression level of hsa-miR-148a-3p)=B3, and if the B3 is greater than or equal to 13.57, Y3=1, and if the B3 is less than 13.57, Y3=0, and (c) Z3 represents a stage of the cancer, and the X3, the Y3, and the Z3 are substituted into equation (3):

$$-10.939+(3.194*X3)+(2.330*Y3)+(2.159*Z3)=N3 \quad \text{equation (3)},$$

whereby the value of N3 is used to determine the prognosis is poor or good.

In various embodiments of the present disclosure, wherein if N3 is greater than or equal to −0.6205, the prognosis is poor, and if N3 is less than −0.6205, the prognosis is good.

In various embodiments of the present disclosure, wherein the specimen includes blood, urine, saliva or ascites.

In various embodiments of the present disclosure, wherein the specimen is obtained after the cancer radiotherapy.

The present disclosure provides the analyzer and the analytical method for predicting the prognosis of cancer radiotherapy, which can be conducted by performing arithmetic operations and determining the prognosis result based on equation (1), equation (2) and equation (3) in accordance with the expression levels of the plurality of miRNAs extracted from the cancer patients before or after radiotherapy. Therefore, the cancer patients can be informed of their prognosis of treatment before or after radiotherapy, providing substantial benefits to the cancer patients.

BRIEF DESCRIPTION OF THE DRAWINGS

The present disclosure can be more fully understood by reading the following detailed description of the embodiment when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides detailed description of many different embodiments, or examples, for implementing different features of the provided subject matter. These are, of course, merely examples and are not intended to limit the invention but to illustrate it. In addition, various embodiments disclosed below may combine or substitute one embodiment with another, and may have additional embodiments in addition to those described below in a beneficial way without further description or explanation. In the following description, many specific details are set forth to provide a more thorough understanding of the present disclosure. It will be apparent, however, to those skilled in the art, that the present disclosure may be practiced without these specific details.

As used herein, the singular forms "a", "an" and "the" are intended to include the plural forms as well, unless expressly stated otherwise. It will be further understood that the terms "includes," "comprises," "including" and/or "comprising,"

when used in this specification, specify the presence of stated features, integers, steps, operations, elements, and/or components, but do not preclude the presence or addition of one or more other features, integers, steps, operations, elements, components, and/or groups thereof.

As described above, currently, about 50% of cancer patients need to receive radiotherapy, including the patients of head and neck cancer and colorectal cancer. In some cases, it is noted that certain tumors are resistant to radiotherapy and prone to recurrence after radiotherapy, and thus result in the poor prognosis.

Accordingly, the present disclosure provides an analyzer and analytical method for predicting a prognosis of cancer radiotherapy, which can be conducted by performing arithmetic operations and determining the prognosis result based on equation (1), equation (2) and equation (3) in accordance with expression levels of a plurality of miRNAs extracted from cancer patients before or after radiotherapy. Therefore, the cancer patients can be informed of their prognosis of treatment before or after radiotherapy.

Figure 1:
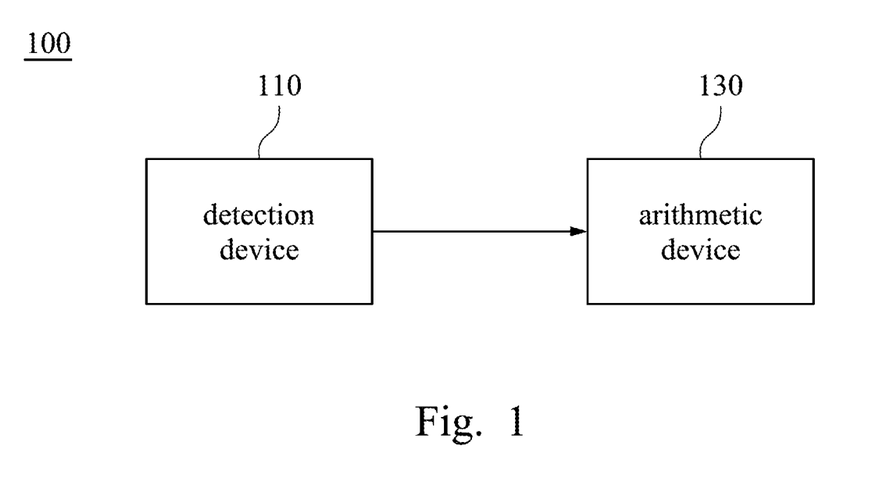
FIG. 1 is an exemplary drawing illustrating an analyzer for predicting a prognosis of cancer radiotherapy in accordance with some embodiments of the present disclosure.

Referring to FIG. 1, FIG. 1 is a drawing schematically illustrating an analyzer for predicting a prognosis of cancer radiotherapy in accordance with some embodiments of the present disclosure. In some embodiments, an analyzer 100 includes a detection device 110 and an arithmetic device 130.

In some embodiments, the detection device 110 can detect the expression levels of the plurality of miRNAs in a specimen, including hsa-miR-130a-3p (SEQ ID NO: 1), hsa-miR-215-5p (SEQ ID NO:2), hsa-miR-29a-3p (SEQ ID NO:3), hsa-let-7b-5p (SEQ ID NO:4), hsa-miR-19b-3p (SEQ ID NO:5), hsa-miR-374a-5p (SEQ ID NO:6) and hsa-miR-148a-3p (SEQ ID NO:7). The detection device 110 can be a qPCR (real-time quantitative polymerase chain reaction) machine. In the reaction of DNA amplification, the qPCR machine can detect the expression level of a product with a fluorescent dye after each PCR cycle.

In some embodiments, the arithmetic device 130 can perform arithmetic operations on the obtained expression levels of the miRNAs, in which the expression level of hsa-miR-215-5p divided by the expression level of hsa-miR-130a-3p equals A, and if the A is less than or equal to 0.09723, X=1, and if the A is greater than 0.09723, X=0; the expression level of hsa-miR-215-5p divided by the expression level of hsa-miR-29a-3p equals B, and if the B is less than or equal to 0.001005, Y=1, and if the B is greater than 0.001005, Y=0; and Z represents a stage of cancer. The X, the Y, and the Z are substituted into equation (1):

$$-99.036+(39.434*X)+(59.996*Y)+(19.636*Z)=N \quad \text{equation (1)}.$$

The value of N is used to determine the prognosis is poor or good.

In some embodiments, the arithmetic device 130 can perform arithmetic operations on the expression levels of the miRNAs, in which the expression level of hsa-miR-130a-3p divided by the expression level of hsa-let-7b-5p equals A2, and if the A2 is greater than or equal to 0.07765, W=1, and if the A2 is less than 0.07765, W=0; the expression level of hsa-miR-130a-3p divided by the expression level of hsa-miR-19b-3p equals B2, and if the B2 is greater than or equal to 0.004635, X2=1, and if the B2 is less than 0.004635, X2=0; the expression level of hsa-miR-130a-3p divided by the expression level of hsa-miR-374a-5p equals C, and if the C is greater than or equal to 0.4640, Y2=1, and if the C is less than 0.4640, Y2=0; and Z2 represents the stage of cancer. The W, the X2, the Y2, and the Z2 are substituted into equation (2):

$$-22.385+(0.113*W)+(18.555*X2)+(1.148*Y2)+(0.997*Z2)=N2 \quad \text{equation (2)}.$$

The value of N2 is used to determine the prognosis is poor or good.

In some embodiments, the arithmetic device 130 can perform arithmetic operations on the expression levels of the miRNAs, in which the expression level of hsa-miR-130a-3p divided by the expression level of hsa-let-7b-5p equals A3, and if the A3 is greater than or equal to 2.041, X3=1, and if the A3 is less than 2.041, X3=0; the expression level of hsa-miR-130a-3p divided by the expression level of hsa-miR-148a-3p equals B3, and if the B3 is greater than or equal to 13.57, Y3=1, and if the B3 is less than 13.57, Y3=0; and Z3 represents the stage of cancer. The X3, the Y3, and the Z3 are substituted into equation (3):

$$-10.939+(3.194*X3)+(2.330*Y3)+(2.159*Z3)=N3 \quad \text{equation (3)}.$$

The value of N3 is used to determine the prognosis is poor or good.

In some embodiments, the arithmetic device 130 can be a computer.

In some embodiments, if N is greater than or equal to −10.51, the prognosis is poor, and if N is less than −10.51, the prognosis is good.

In some embodiments, if N2 is greater than or equal to 0.2145, the prognosis is poor, and if N2 is less than 0.2145, the prognosis is good.

In some embodiments, if N3 is greater than or equal to −0.6205, the prognosis is poor, and if N3 is less than −0.6205, the prognosis is good.

In some embodiments, the arithmetic device 130 includes output devices. The output devices include a display screen, a printer, a voice system or combinations thereof. Therefore, the calculated value (N, N2 or N3) by equation (1), equation (2) or equation (3) may appear on the display screen or printed paper, or the value of N, N2 or N3 may be directly articulated by the voice system.

More specifically, signal transmission between the detection device 110 and the arithmetic device 130 may be implemented via wired or wireless means, but not limited thereto. In some embodiments, the detection device 110 is electrically connected to the arithmetic device 130 for signal transmission. In another embodiment, signal transmission between the detection device 110 and the arithmetic device 130 may be implemented via infrared or Bluetooth.

Extracted from a patient, the specimen described above may include blood, urine, saliva or ascites. In some embodiments, when the equation (1) and the equation (2) are used for predicting the prognosis, the specimen from the patient is extracted before radiotherapy. In some embodiments, when the equation (3) is used for predicting the prognosis, the specimen from the patient is extracted after radiotherapy.

Figure 2:
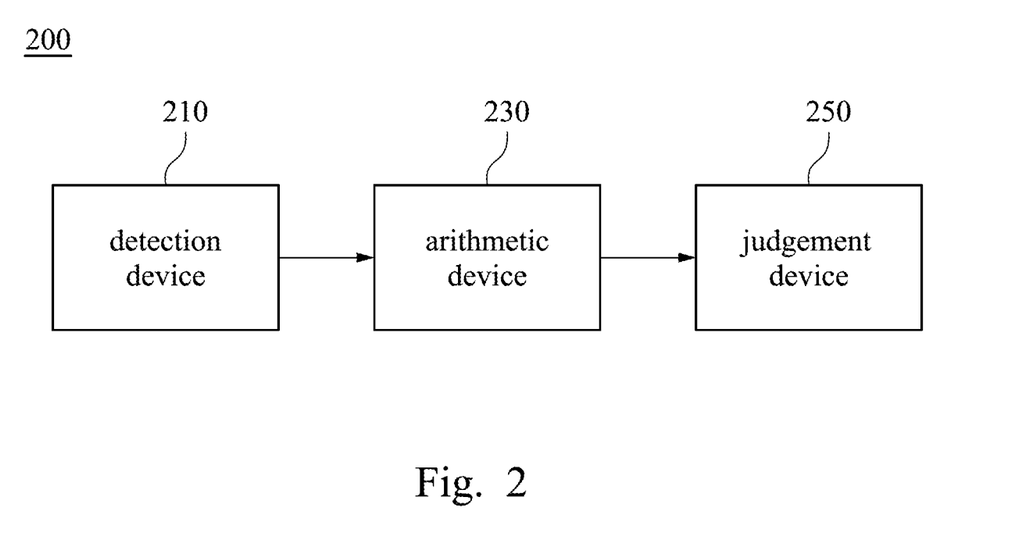
FIG. 2 is an exemplary drawing illustrating another analyzer for predicting a prognosis of cancer radiotherapy in accordance with some embodiments of the present disclosure.

Referring to FIG. 2 is an exemplary drawing illustrating an analyzer for predicting a prognosis of cancer radiotherapy in accordance with some embodiments of the present disclosure. In some embodiments, an analyzer 200 includes a detection device 210, an arithmetic device 230 and a judgment device 250. Description of the detection device 210 and the arithmetic device 230 may refer to the detection device 110 and the arithmetic device 130 mentioned above in connection with FIG. 1, and is not repetitively described herein.

In some embodiments, on the basis of the value of N, N2 or N3 calculated by the arithmetic device 230, the judgment device 250 may determine that the patient has a good prognosis or a poor prognosis. In some embodiments, the judgment device 250 may further generate a receiver operating characteristic (ROC) curve and calculate the area under curve (AUC), by weighting the expression levels of the plurality of miRNAs described above. AUC=0.5 represents no discrimination; 0.7≤AUC≤0.8 represents acceptable discrimination; 0.8≤AUC≤0.9 represents excellent discrimination; and 0.9≤AUC≤1.0 represents outstanding discrimination. Accordingly, AUC is used for determining the discriminatory capacity of equations in the present disclosure.

In some embodiments, signal transmission among the detection device 210, the arithmetic device 230 and the judgment device 250 may be implemented via wired or wireless means, but not limited thereto. In some embodiments, the detection device 210, the arithmetic device 230 and the judgment device 250 are electrically connected to each other for signal transmission. In another embodiment, signal transmission among the detection device 110, the arithmetic device 130 and the judgment device 250 may be transmitted via infrared or Bluetooth.

The present disclosure also provides an analytical method for predicting a prognosis of cancer radiotherapy, including: obtaining a plurality of miRNAs from a specimen; performing arithmetic operations on expression levels of the plurality of miRNAs to yield a calculated value (i.e. N, N2 or N3); and determining the prognosis is good or poor based on the calculated value of arithmetic operations.

Figure 3:
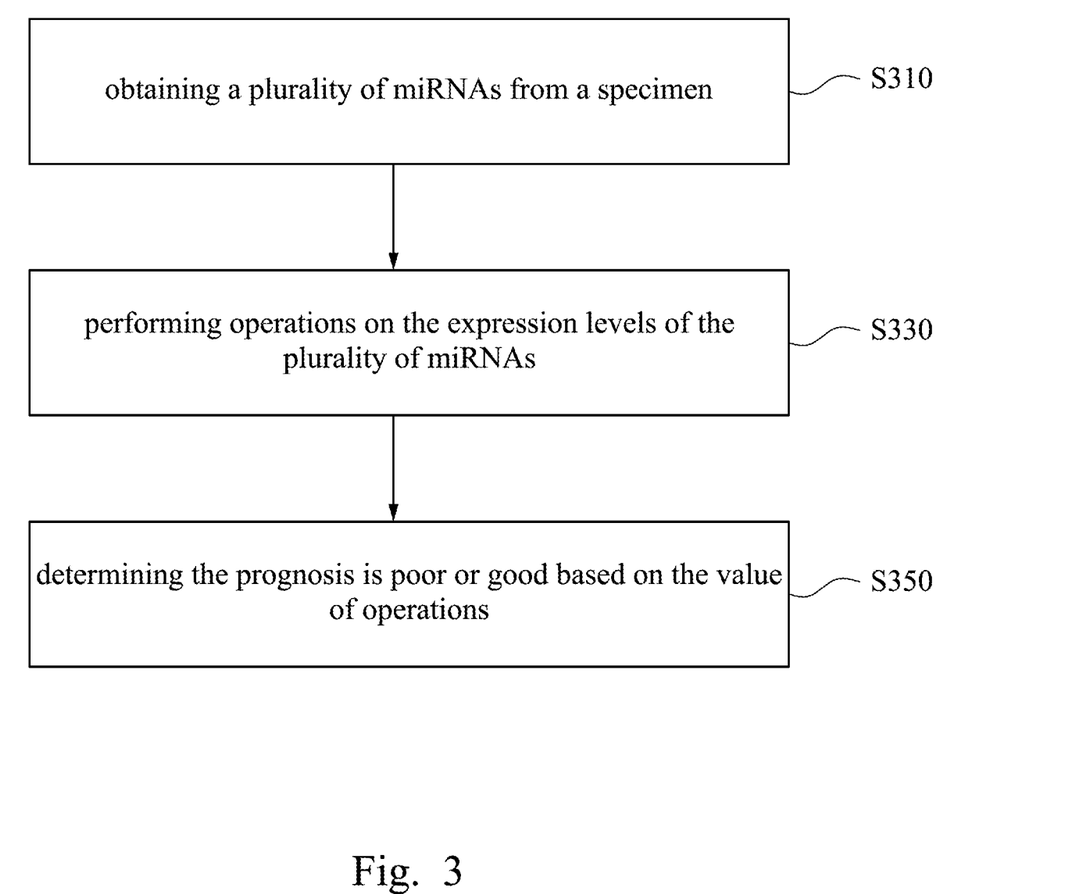
FIG. 3 is a flow chart illustrating an analytical method for predicting a prognosis of cancer radiotherapy in accordance with some embodiments of the present disclosure.

Referring to FIG. 3, FIG. 3 is a flow chart illustrating the analytical method for predicting a prognosis of cancer radiotherapy in accordance with some embodiments of the present disclosure.

In step 310, the plurality of miRNAs is obtained from the specimen. In some embodiments, the plurality of miRNAs includes hsa-miR-130a-3p (SEQ ID NO:1), hsa-miR-215-5p (SEQ ID NO:2) and hsa-miR-29a-3p (SEQ ID NO:3). In some embodiments, the plurality of miRNAs includes hsa-miR-130a-3p (SEQ ID NO:1), hsa-let-7b-5p (SEQ ID NO:4), hsa-miR-19b-3p (SEQ ID NO:5) and hsa-miR-374a-5p (SEQ ID NO:6). In some embodiments, the plurality of miRNAs includes hsa-miR-130a-3p (SEQ ID NO: 1), hsa-let-7b-5p (SEQ ID NO:4) and hsa-miR-148a-3p (SEQ ID NO:7). In some embodiments, the plurality of miRNAs may be obtained by conventional miRNA extraction methods or the protocol of commercial Ambion mirVana miRNA Isolation Kit.

In some embodiments, the specimen includes blood, saliva or ascites extracted from a patient. In some embodiments, when the plurality of miRNAs used for predicting the prognosis are hsa-miR-130a-3p (SEQ ID NO:1), hsa-miR-215-5p (SEQ ID NO:2), and hsa-miR-29a-3p (SEQ ID NO:3), the specimen from the patient is extracted before radiotherapy. In some embodiments, when the plurality of miRNAs used for predicting the prognosis are hsa-miR-130a-3p (SEQ ID NO:1), hsa-let-7b-5p (SEQ ID NO:4), hsa-miR-19b-3p (SEQ ID NO:5), and hsa-miR-374a-5p (SEQ ID NO:6), the specimen from the patient is extracted before radiotherapy. In some embodiments, when the plurality of miRNAs used for predicting the prognosis are hsa-miR-130a-3p (SEQ ID NO:1), hsa-let-7b-5p (SEQ ID NO:4), and hsa-miR-148a-3p (SEQ ID NO:7), the specimen from the patient is extracted after radiotherapy.

In step 330, arithmetic operations are performed on the expression levels of the plurality of miRNAs to obtain the calculated value. In some embodiments, (the expression level of hsa-miR-215-5p)/(the expression level of hsa-miR-130a-3p)=A, and if the A is less than or equal to 0.09723, X=1, and if the A is greater than 0.09723, X=0; (the expression level of hsa-miR-215-5p)/(the expression level of hsa-miR-29a-3p)=B, and if the B is less than or equal to 0.001005, Y=1, and if the B is greater than 0.001005, Y=0; and Z represents a stage of the cancer. The X, the Y, and the Z are substituted into equation (1):

$$-99.036+(39.434*X)+(59.996*Y)+(19.636*Z)=N \qquad \text{equation (1)}.$$

The value of N is used to determine the prognosis is poor or good.

In some embodiments, (the expression level of hsa-miR-130a-3p)/(the expression level of hsa-let-7b-5p)=A2, and if the A2 is greater than or equal to 0.07765, W=1, and if the A2 is less than 0.07765, W=0; (the expression level of hsa-miR-130a-3p)/(the expression level of hsa-miR-19b-3p) =B2, and if the B2 is greater than or equal to 0.004635, X2=1, and if the B2 is less than 0.004635, X2=0; (the expression level of hsa-miR-130a-3p)/(the expression level of hsa-miR-374a-5p)=C, and if the C is greater than or equal to 0.4640, Y2=1, and if the C is less than 0.4640, Y2=0; and Z2 represents a stage of the cancer. The W, the X2, the Y2, and the Z2 are substituted into equation (2):

$$-22.385+(0.113*W)+(18.555*X2)+(1.148*Y2)+(0.997*Z2)=N2 \qquad \text{equation (2)}$$

The value of N2 is used to determine the prognosis is poor or good.

In some embodiments, (the expression level of hsa-miR-130a-3p)/(the expression level of hsa-let-7b-5p)=A3, and if the A3 is greater than or equal to 2.041, X3=1, and if the A3 is less than 2.041, X3=0; (the expression level of hsa-miR-130a-3p)/(the expression level of hsa-miR-148a-3p)=B3, and if the B3 is greater than or equal to 13.57, Y3=1, and if the B3 is less than 13.57, Y3=0; and Z3 represents a stage of the cancer. The X3, the Y3, and the Z3 are substituted into equation (3):

$$-10.939+(3.194*X3)+(2.330*Y3)+(2.159*Z3)=N3 \qquad \text{equation (3)}$$

The value of N3 is used to determine the prognosis is poor or good.

In some embodiments, before the arithmetic operations, the analytical method further includes a step for detecting the expression levels of the plurality of miRNAs. First, if the specimen in step 310 is extracted before radiotherapy, for example, specific primers are used for reverse transcription to synthesize complementary DNAs (cDNAs) of hsa-miR-130a-3p, hsa-miR-215-5p, hsa-miR-29a-3p, hsa-let-7b-5p, hsa-miR-19b-3p and hsa-miR-374a-5p. Next, in amplification reaction, fluorescent probes are used to detect cDNAs of hsa-miR-130a-3p, hsa-miR-215-5p, hsa-miR-29a-3p, hsa-let-7b-5p, hsa-miR-19b-3p and hsa-miR-374a-5p, via fluorescent emission. As the amplification cycles increase, the fluorescent signals become stronger and thus quantification of the fluorescence intensity is carried out. In some embodiments, if the specimen in step 310 is extracted after radiotherapy, the expression levels of hsa-miR-130a-3p, hsa-let-7b-5p and hsa-miR-148a-3p can be quantified in accordance with the detection steps described above.

In step 350, a poor prognosis or a good prognosis is determined based on the calculated value. In some embodiments, if N is greater than or equal to −10.51, the prognosis is poor, and if N is less than −10.51, the prognosis is good. In some embodiments, if N2 is greater than or equal to 0.2145, the prognosis is poor, and if N2 is less than 0.2145, the prognosis is good. In some embodiments, if N3 is greater than or equal to −0.6205, the prognosis is poor, and if N3 is less than −0.6205, the prognosis is good.

Last but not least, after the test subject receiving radiotherapy, medical personnel may observe cancer lesions in the test subject using computed tomography (CT), nuclear magnetic resonance imaging (NMRI), positron emission tomography (PET), tumor markers or combinations thereof. Accordingly, clinical response is measured by response evaluation criteria in solid tumor (RECIST), and the RECIST can be divided into the complete response (CR), partial response (PR) or progressive disease (PD), to the radiotherapy. The aforementioned good prognosis corresponds to the CR or PR. The aforementioned poor prognosis corresponds to the PD. Therefore, the prognosis result (obtained by using embodiments described above) can be validated when comparing with the actual outcome (clinical response).

More specifically, the RECIST uses tumor length as its criteria for measurement. "Complete response" is defined as complete disappearance of tumor, and the complete disappearance shall be confirmed again 4 weeks later. "Partial response" is defined as at least a 30% decrease in the sum of the longest diameter (LD). "Progressive disease" is defined as at least a 20% increase in the sum of the LD and the absolute value of the increase greater than 5 millimeters (mm), or the appearance of new lesion.

An embodiment is provided hereinafter. In accordance with the present disclosure, the embodiment used the equations to analyze prognosis of patients receiving cancer radiotherapy. Specimens of the embodiment were blood samples from 27 test subjects suffered from head and neck cancer or colorectal cancer. The head and neck cancer included tonsil cancer, nasopharynx cancer, hypopharyngeal cancer, soft palate cancer, oropharyngeal cancer, laryngeal cancer, tongue cancer, and head and neck tumors. The colorectal cancer included sigmoid colon cancer, rectal cancer, and anal cancer. For patients with head and neck cancer and colorectal cancer, tumors are often unable to be removed by surgery, and thus radiotherapy has become one of the most common treatments for such patients. Accordingly, if one can predict the prognosis of patients before receiving radiotherapy, the medical personnel may choose more suitable treatment for the patients in reference to the prognosis result and therefore provide instant and substantial assistance to the patients.

First, blood was collected from each test subject before and after radiotherapy, and then the plasma was separated from each of the blood samples. Next, miRNAs were extracted from the plasma and absorption 260/280 ratios of the extracted miRNAs ranged from about 1.5 to 1.6. For miRNAs detection, 0.5 µg miRNAs per PCR was sufficient.

Then, for the specimen obtained before radiotherapy, reverse transcription for the miRNAs was carried out to synthesize complementary DNAs (cDNAs) of hsa-miR-130a-3p, hsa-miR-215-5p, hsa-miR-29a-3p, hsa-let-7b-5p, hsa-miR-19b-3p and hsa-miR-374a-5p. Next, in amplification reaction, the fluorescent probes were used to detect cDNAs of hsa-miR-130a-3p, hsa-miR-215-5p, hsa-miR-29a-3p, hsa-let-7b-5p, hsa-miR-19b-3p and hsa-miR-374a-5p, via fluorescent emission. As the amplification cycles increased, the fluorescent signals became stronger and thus Ct (threshold cycle) values of cDNAs of hsa-miR-130a-3p, hsa-miR-215-5p, hsa-miR-29a-3p, hsa-let-7b-5p, hsa-miR-19b-3p and hsa-miR-374a-5p, were determined based on quantification of fluorescence intensity. By subtracting Ct values of highly conserved RNU6 or RNU48 from the Ct values of cDNAs of hsa-miR-130a-3p, hsa-miR-215-5p, hsa-miR-29a-3p, hsa-let-7b-5p, hsa-miR-19b-3p and hsa-miR-374a-5p, $\Delta CT1$, $\Delta CT2$, $\Delta CT3$, $\Delta CT4$, $\Delta CT5$ and $\Delta CT6$ were obtained, respectively. Accordingly, for the specimen obtained before radiotherapy, the expression level of hsa-miR-130a-3p was expressed as $2^{-\Delta CT1}$; the expression level of hsa-miR-215-5p was expressed as $2^{-\Delta CT2}$; the expression level of hsa-miR-29a-3p was expressed as $2^{-\Delta CT3}$; the expression level of hsa-let-7b-5p was expressed as $2^{-\Delta CT4}$; the expression level of hsa-miR-19b-3p was expressed as $2^{-\Delta CT5}$; and the expression level of hsa-miR-374a-5p was expressed as $2^{-\Delta CT6}$.

For the specimen obtained after radiotherapy, the expression levels of hsa-miR-130a-3p, hsa-let-7b-5p and hsa-miR-148a-3p were detected by using the same analytical method described above, and $\Delta CT7$, $\Delta CT8$ and $\Delta CT9$ were obtained, respectively. Accordingly, for the specimen obtained after radiotherapy, the expression level of hsa-miR-130a-3p was expressed as $2^{-\Delta CT7}$; the expression level of hsa-let-7b-5p was expressed as $2^{-\Delta CT8}$; and the expression level of hsa-miR-148a-3p was expressed as $2^{-\Delta CT9}$.

Next, in the cases where the specimens were obtained before radiotherapy, the expression level of hsa-miR-130a-3p, the expression level of hsa-miR-215-5p, the expression level of hsa-miR-29a-3p, the expression level of hsa-let-7b-5p, the expression level of hsa-miR-19b-3p and the expression level of hsa-miR-374a-5p were substituted into equation (1) and equation (2); and in the case where the specimens were obtained after radiotherapy, the expression level of hsa-miR-130a-3p, the expression level of hsa-let-7b-5p and the expression level of hsa-miR-148a-3p were substituted into equation (3). Accordingly, arithmetic operations were performed to obtain calculated values and then the calculated values were used to determine the prognosis of test subjects.

Besides, six months after the radiotherapy, the medical personnel used computer tomography (CT) to determine the clinical responses of test subjects. Compared it with the prognosis results based on the equations herein, it was found that the analyzer and analytical method provided by the present disclosure has outstanding discrimination level.

ROC curves were illustrated using PRISM software for further embodying the discrimination level of the analyzer and analytical method of the present disclosure. All input data were the expression levels of the present embodiment and analyzed with default settings. The maximum sum of sensitivity and specificity were used as the cut-off value. Sensitivity, specificity, and accuracy (discrimination level) were obtained, as shown in FIG. 4-6.

Figure 4:
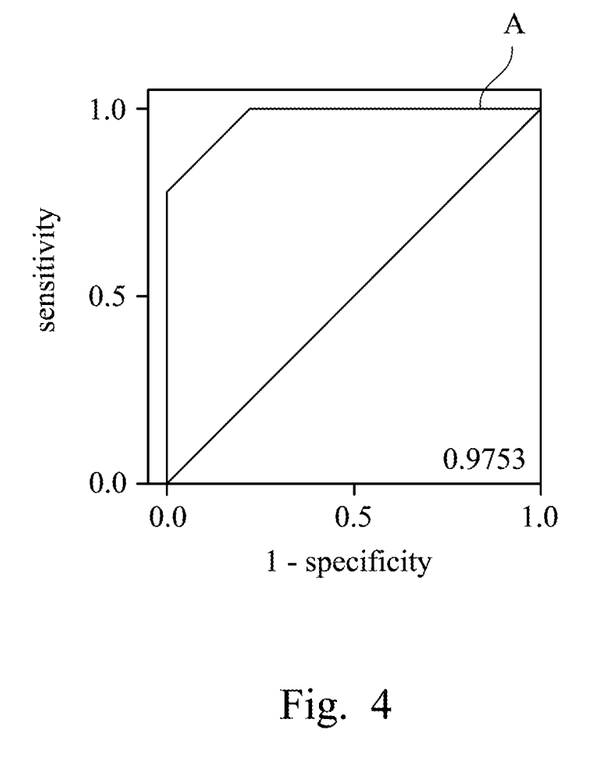
FIG. 4 is a graph depicting a ROC curve in accordance with some embodiments of the present disclosure.
Figure 5:
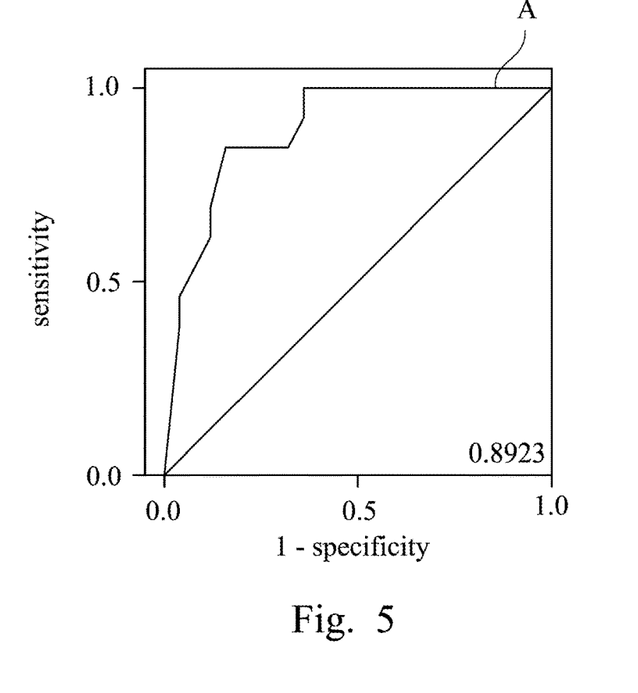
FIG. 5 is a graph depicting a ROC curve in accordance with some embodiments of the present disclosure.
Figure 6:
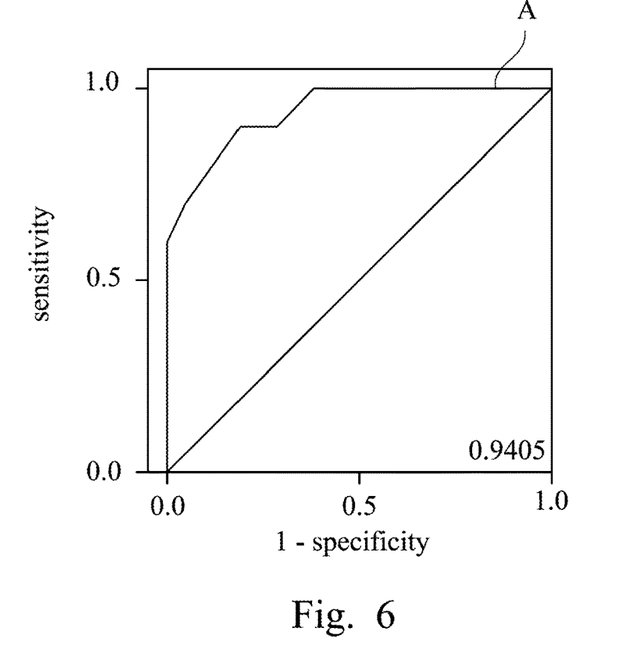
FIG. 6 is a graph depicting a ROC curve in accordance with some embodiments of the present disclosure.

Referring to FIG. 4 to FIG. 6, FIG. 4 to FIG. 6 are graphs depicting ROC curves in accordance with some embodiments of the present disclosure. The "sensitivity" of vertical axis represents poor actual outcomes and the test subjects are also determined as poor prognoses by using the analyzer and analytical method of the present disclosure before/after radiotherapy (true positive). The "1—specificity" of horizontal axis represents good actual outcomes and the test subjects are determined as poor prognoses by using the analyzer and analytical method of the present disclosure before/after radiotherapy (false positive). "Specificity" represents good actual outcomes and the test subjects are determined as good prognoses by using the analyzer and analytical method of the present disclosure before/after radiotherapy.

As shown in FIG. 4, the prognosis result is analyzed using equation (1) before radiotherapy, and the value of AUC under ROC curve A is 0.9753. On the basis of the criteria described above, $0.9 \leq AUC \leq 1.0$ represents outstanding discrimination. Accordingly, it is validated that the analyzer and analytical method provided by the present disclosure exhibit outstanding discrimination.

As shown in FIG. 5, the prognosis result is analyzed using equation (2) before radiotherapy, and the value of AUC under ROC curve A is 0.8923. On the basis of the criteria described above, 0.8≤AUC≤0.9 represents excellent discrimination. Accordingly, it is validated that the analyzer and analytical method provided by the present disclosure exhibit excellent discrimination.

Further referring FIG. 6, the prognosis result is analyzed using equation (3) after radiotherapy, and the value of AUC under ROC curve A is 0.9405. On the basis of the criteria described above, 0.9≤AUC≤1.0 represents outstanding discrimination. Accordingly, it is validated that the analyzer and analytical method provided by the present disclosure exhibit outstanding discrimination.

According to the embodiments of the present disclosure described above, the present disclosure provides an analyzer and analytical method for predicting a prognosis of cancer radiotherapy and has advantages over the prior art. The advantages are summarized as follows. The analyzer and analytical method of the present disclosure may predict prognoses of patients receiving radiotherapy, before or after radiotherapy. Therefore, the cancer patients can be informed of their prognosis of treatment before or after radiotherapy. The medical personnel may choose more suitable treatment for the patients in reference to the prognosis result and therefore provide instant and substantial assistance to the patients. Besides, used in the analyzer and analytical method of the present disclosure, the specimen can be easily and conveniently obtained. It may reduce the probability that cancer patients receive unsuitable treatments and has a low-cost advantage.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An analyzer for predicting a prognosis of cancer radiotherapy, comprising:
- a detection device that detects in a specimen miRNAs comprising hsa-miR-130a-3p (SEQ ID NO:1), hsa-miR-215-5p (SEQ ID NO:2) and hsa-miR-29a-3p (SEQ ID NO:3);
- an arithmetic device configured to perform arithmetic operations on expression levels of the miRNAs, wherein (a) the expression level of hsa-miR-215-5p divided by the expression level of hsa-miR-130a-3p equals A, and if the A is less than or equal to 0.09723, X=1, and if the A is greater than 0.09723, X=0, (b) the expression level of hsa-miR-215-5p divided by the expression level of hsa-miR-29a-3p equals B, and if the B is less than or equal to 0.001005, Y=1, and if the B is greater than 0.001005, Y=0, and (c) Z represents a stage of the cancer, and the X, the Y, and the Z are substituted into equation (1):

$$-99.036+(39.434*X)+(59.996*Y)+(19.636*Z)=N \quad \text{equation (1),}$$

whereby the value of N is used to determine the prognosis is poor or good; and
- a judgment device configured to determine a prognosis result and advise a patient of the specimen with a suitable therapy based on the prognosis result.

2. The analyzer of claim 1,
wherein if N is greater than or equal to −10.51, the prognosis is poor, and if N is less than −10.51, the prognosis is good.

3. An analyzer for predicting a prognosis of cancer radiotherapy, comprising:
- a detection device that detects in a specimen miRNAs comprising hsa-miR-130a-3p (SEQ ID NO:1), hsa-let-7b-5p (SEQ ID NO:4), hsa-miR-19b-3p (SEQ ID NO:5) and hsa-miR-374a-5p (SEQ ID NO:6),
- an arithmetic device configured to perform on arithmetic operations on expression levels of the miRNAs, wherein (a) the expression level of hsa-miR-130a-3p divided by the expression level of hsa-let-7b-5p equals A2, and it the A2 is greater than or equal to 0.07765, W=1, and if the A2 is less than 0.07765, W=0, (b) the expression level of hsa-miR-130a-3p divided by the expression level of hsa-miR-19b-3p equals B2, and if the B2 is a greater than or equal to 0.004635, X2=1, and if the B2 is less than 0.004635, X2=0, (c) the expression level of hsa-miR-130a-3p divided by the expression level of hsa-miR-374a-5p equals C, and if the C is greater than or equal to 0.4640, Y2=1, and if the C is less than 0.4640, Y2=0, and (d) Z2 represents a stage of the cancer, and the W, the X2, the Y2, and the Z2 are substituted into equation (2):

$$-22.385+(0.113*W)+(18.555*X2)+(1.148*Y2)+(0.997*X2)=N2 \quad \text{equation (2),}$$

whereby the value of N2 is used to determine the prognosis is poor or good; and
- a judgment device configured to determine a prognosis result and advise a patient of the specimen with a suitable therapy based on the prognosis result.

4. The analyzer of claim 3,
wherein if N2 is greater than or equal to 0.2145, the prognosis is poor, and if N2 is less than 0.2145, the prognosis is good.

5. The analyzer of claim 3, wherein the specimen comprises blood, urine, saliva or ascites.

6. The analyzer of claim 3, wherein the specimen is obtained before the cancer radiotherapy.

7. An analytical method for predicting a prognosis of cancer radiotherapy, comprising:
- obtaining a plurality of miRNAs from a specimen, wherein the plurality of miRNAs comprises hsa-miR-130a-3p (SEQ ID NO:1), hsa-let-7b-5p (SEQ ID NO:4), hsa-miR-19b-3p (SEQ ID NO:5) and hsa-miR-374a-5p (SEQ ID NO:6);
- detecting expression levels of the plurality of miRNAs from the specimen;
- performing arithmetic operations on the expression levels of the plurality of miRNAs, wherein (a) (the expression level of hsa-miR-130a-3p)/(the expression level of hsa-let-7b-5p)=A2, and if the A2 is greater than or equal to 0.07765, W=1, and if the A2 is less than 0.07765, W=0, (b) (the expression level of hsa-miR-130a-3p)/(the expression level of hsa-miR-19b-3p)=B2, and if the B2 is greater than or equal to 0.004635, X2=1, and if the B2 is less than 0.004635, X2=0, (c) (the expression level of hsa-miR-130a-3p)/(the expression level of hsa-miR-374a-5p)=C, and if the C is greater than or equal to 0.4640, Y2=1, and if the C is less than 0.4640, Y2=0 and (d) Z2 represents a stage of the cancer, and the W, the X2, the Y2, and the Z2 are substituted into equation (2):

$$-22.385+(0.113*W)+(18.555*X2)+(1.148*Y2)+(0.997*X2)=N2 \quad \text{equation (2),}$$

whereby the value of N2 is used to determine the prognosis is poor or good; and treating a patient of the specimen with a suitable therapy based on the prognosis result.

8. The method of claim 7,
wherein if N2 is greater than or equal to 0.2145, the prognosis is poor, and if N2 is less than 0.2145, the prognosis is good.

9. The method of claim 7, wherein the specimen comprises blood, urine, saliva or ascites.

10. The method of claim 7, wherein the specimen is obtained before the cancer radiotherapy.

11. An analyzer for predicting a prognosis of cancer radiotherapy, comprising:
a detection device that detects in a specimen miRNAs comprising hsa-miR-130a-3p (SEQ ID NO:1), hsa-let-7b-5p (SEQ ID NO:4) and hsa-miR-148a-3p (SEQ ID NO:7);
an arithmetic device configured to perform arithmetic operations on expression levels of the miRNAs, wherein (a) the expression level of hsa-miR-130a-3p divided by the expression level of hsa-miR-7b-5p equals A3, and if the A3 is greater than or equal to 2.041, X3=1, and if the A3 is less than 2.041, X3=0, (b) the expression level of hsa-miR-130a-3p divided by the expression level of hsa-miR-148a-3p equals B3, and if the B3 is greater than or equal to 13.57, Y3=1, and if the B3 is less than 13.57, Y3=0, and (c) Z3 represents a stage of the cancer, and the X3, the Y3, and the Z3 are substituted into equation (3):

$$-10.939+(3.194*X3)+(2.330*Y2)+(2.159*Z3)=N3 \quad \text{equation (3)},$$

whereby the value of N3 is used to determine the prognosis is poor or good; and
a judgment device configured to determine a prognosis result and advising a patient of the specimen with a suitable therapy based on the prognosis result.

12. The analyzer of claim 11,
wherein if N3 is greater than or equal to −0.6205, the prognosis is poor, and if N3 is less than −0.6205, the prognosis is good.

13. The analyzer of claim 11, wherein the specimen comprises blood, urine, saliva or ascites.

14. The analyzer of claim 11, wherein the specimen is obtained after the cancer radiotherapy.

15. An analytical method for predicting a prognosis of cancer radiotherapy, comprising:
obtaining a plurality of miRNAs from a specimen, wherein the plurality of miRNAs comprises hsa-miR-130a-3p (SEQ ID NO:1), hsa-let-7b-5p (SEQ ID NO:4) and hsa-miR-148a-3p (SEQ ID NO:7);
detecting expression levels of the plurality of miRNAs from the specimen;
performing arithmetic operations on the expression levels of the plurality of miRNAs, wherein (a) (the expression level of hsa-miR-130a-3p)/(the expression level of hsa-let-7b-5p)=A3, and if the A3 is greater than or equal to 2.041, X3=1, and if the A3 is less than 2.041, X3=0, (b) (the expression level of hsa-miR-130a-3p)/(the expression level of hsa-miR-148b-3p)=B3, and if the B3 is greater than or equal to 13.57, Y3=1, and if the B3 is less than 13.57, Y3=0, and (c) Z3 represents a stage of the cancer, and the X3, the Y3, and the Z3 are substituted into equation (3):

$$-10.939+(3.194*X3)+(2.330*Y2)+(2.159*Z3)=N3 \quad \text{equation (3)},$$

whereby the value of N3 is used to determine the prognosis is poor or good; and
treating a patient of the specimen with a suitable therapy based on the prognosis result.

16. The analytic method of claim 15,
wherein if N3 is greater than or equal to −0.6205, the prognosis is poor, and if N3 is less than −0.6205, the prognosis is good.

17. The analytic method of claim 15, wherein the specimen comprises blood, urine, saliva or ascites.

18. The analytic method of claim 15, wherein the specimen is obtained after the cancer radiotherapy.

* * * * *

SEQUENCE LISTING

<160> NUMBER OF SEQ ID NOS: 7

<210> SEQ ID NO 1
<211> LENGTH: 22
<212> TYPE: RNA
<213> ORGANISM: Homo sapiens

<400> SEQUENCE: 1
cagugcaaug uuaaaagggc au                                        22

<210> SEQ ID NO 2
<211> LENGTH: 21
<212> TYPE: RNA
<213> ORGANISM: Homo sapiens

<400> SEQUENCE: 2
augaccuaug aauugacaga c                                         21

<210> SEQ ID NO 3
<211> LENGTH: 22
<212> TYPE: RNA
<213> ORGANISM: Homo sapiens

<400> SEQUENCE: 3
uagcaccauc ugaaaucggu ua                                        22

<210> SEQ ID NO 4
<211> LENGTH: 22
<212> TYPE: RNA
<213> ORGANISM: Homo sapiens

<400> SEQUENCE: 4
ugagguagua gguugugugg uu                                        22

<210> SEQ ID NO 5
<211> LENGTH: 23
<212> TYPE: RNA
<213> ORGANISM: Homo sapiens

<400> SEQUENCE: 5
ugugcaaauc caugcaaaac uga                                       23

```
<210> SEQ ID NO 6
<211> LENGTH: 22
<212> TYPE: RNA
<213> ORGANISM: Homo sapiens

<400> SEQUENCE: 6
uuauaauaca accugauaag ug                                              22

<210> SEQ ID NO 7
<211> LENGTH: 22
<212> TYPE: RNA
<213> ORGANISM: Homo sapiens

<400> SEQUENCE: 7
ucagugcacu acagaacuuu gu                                              22
```